United States Patent [19]

Knuettel et al.

[11] Patent Number: 4,490,675
[45] Date of Patent: Dec. 25, 1984

[54] ELECTROMAGNET FOR USE IN NMR TOMOGRAPHY

[75] Inventors: Bertold Knuettel; Günther Laukien, both of Rheinstetten, Fed. Rep. of Germany

[73] Assignee: Bruker Analytische Messtechnik GmbH, Rheinstetten-Forchheim, Fed. Rep. of Germany

[21] Appl. No.: 386,981

[22] Filed: Jun. 10, 1982

[30] Foreign Application Priority Data

Jun. 13, 1981 [DE] Fed. Rep. of Germany ....... 3123493

[51] Int. Cl.$^3$ ............................................. G01R 33/08
[52] U.S. Cl. ..................................... 324/319; 324/318
[58] Field of Search ........................ 324/300, 318–320, 324/316, 303

[56] References Cited

U.S. PATENT DOCUMENTS

| 4,048,555 | 9/1977 | Rupp | 324/320 |
| 4,354,499 | 10/1982 | Damadian | 324/309 |
| 4,390,494 | 6/1983 | Sallsbury | 324/319 |

Primary Examiner—Michael J. Tokar
Attorney, Agent, or Firm—Burmeister, York, Palmatier, Hamby & Jones

[57] ABSTRACT

An electromagnet for producing the constant magnetic field required for use in NMR tomography consists of a cylindrical field coil and a stable cylindrical shell made of iron encompassing and simultaneously supporting the coil. The field coil may comprise constituent coils, including error coils, and is capable of producing an at least approximately homogeneous magnetic field within the space defined by the field coil for receiving the object to be examined. Due to the strictly symmetric geometry of the coil assembly, the homogeneity of the magnetic field is not adversely affected by temperature fluctuations, even if the dimensions of the apparatus are such that the coil will admit a human body. The cylindrical shell, however, does not only serve as an extremely stable supporting means, but also forms the vehicle for a magnetic reflux by which the energy requirements of the magnet are considerably reduced, and further, also constitutes shielding means both against external magnetic fields and electromagnetic interference and radiation from the high frequency field produced in NMR tomography. The cylindrical iron shell may be provided at its end portions with operational members such as annular discs and tubular studs and may be closed by iron covers, so that its effectiveness may even be further enhanced.

20 Claims, 6 Drawing Figures

ELECTROMAGNET FOR USE IN NMR TOMOGRAPHY

FIELD OF THE INVENTION

This invention relates to an electromagnet for producing the constant magnetic field required for use in NMR tomography. The electromagnet includes a coil assembly to generate an at least approximately homogeneous magnetic field inside the space defined by the coil assembly and prepared to receive the organic body presented for examination.

BACKGROUND OF THE INVENTION

It has been found that NMR spectroscopy is capable of producing cross-sectional images of organic bodies and is of particular value in the medical examination of the human body. Experiments in this field have been conducted previously and devices suitable for the stated purpose have been developed (Nachr. Chem. Tec. Lab. 28 (1980), No. 12, p. 860–865). This method of producing cross-sectional body images is generally referred to as NMR tomography, occasionally also as NMR Zeugmatography or NMR Imaging.

A considerable problem in NMR tomography is related to the production of a homogeneous magnetic field of the dimensions required to accommodate the section of a body being examined. In view of an expenditure that can be reasonably justified, the production of homogeneous magnetic fields of a size necessary for the examination in psrticular of the human body may probably have to be confined to the interior of current carrying coils because permanent electromagnets with pole pieces of sufficient size separated by an appropriately large distance would be too elaborate and especially much too heavy. Thus, the reference cited in the foregoing utilizes an electromagnet for NMR tomography which comprises four water cooled current carrying coils arranged in what is known as a Helmholtz Double Coil assembly.

To create homogeneous magnetic fields by means of such constituent coil assemblies necessitates an extremely accurate dimensioning and setting of the constituent coils to meet the high requirements as to homogeneity of the magnetic field and eliminate by way of compensation any interfering field components of a higher order. Even minor positional changes may adversely affect any such compensation and, consequently, the homogeneity of the magnetic field. Positional changes may easily occur due to different heat expansion of the elements forming the supporting structure for the coils. For this reason, when such compound coils are put to use in laboratories etc., care is being taken to ensure a constant room temperature. Any disturbing influences are, of course, the greater, the larger the coils are. In NMR tomography, extremely large coil arrangements are required in the examination of an organic body, be it human or animal, which must fit into the space encompassed by the coils. The minimum interior diameter of a coil to be used in the examination of the human body is approximately 650 mm.

A further source of error is the effect of external magnetic fields. While it is possible in principle to shield the rooms housing NMR apparatus from external magnetic fields, such protective measures involve a high degree of technical expenditure.

Another problem connected with NMR tomography is that the coils required to produce the high frequency magnetic field must likewise be of a large diameter. This has the effect that the coils act to a considerable degree as transmitting antennas, giving rise to substantial disturbances, especially, if standing waves are developing in the work room which may cause great localized fluctuations in the field strength of the HF field. Moreover, there is an appreciable loss of energy, and the sensitivity of the apparatus is also affected.

In addition to the adverse effect on the NMR tomography, radiation from a high frequency field may also affect electromagnetic devices stationed in the same room with the coils. This is true especially of peripheral devices required for use in conjunction with NMR tomography such as, for example, memory discs, floppy discs, etc.

In the prior art electromagnets, the current load on the coils and thus the power requirements are extremely high. Cooling means are usually necessary of a magnitude that not only involves substantial expenditures, but which also may be the cause for the creation of temperature gradients. These, in turn, may lead to varying heat expansion values, so that changes in the geometric arrangement of the structural elements may be necessary which are not to the best in an electromagnet of this type and, as previously indicated, may result in disturbances in the homogeneity of the magnetic field.

All of these problems appear to make it nearly impossible to produce an electromagnet which is insensitive to disturbances to the extent that it can be successfully used at the office of a radiologist, in diagnostic departments of hospitals, and in other zoological or biological institutions, and which at the same time is of a structurally simple design and easy to manufacture, with sufficiently small dimensions and low energy requirements to be suitable for practical application in the field.

The present invention has as its object to create an electromagnet of the afore-mentioned type.

SUMMARY OF THE INVENTION

This is accomplished according to the invention by providing an electromagnet which comprises a cylindrical field coil enclosed in and supported by a stable cylindrical shell made of iron.

The electromagnet according to the invention makes use of a relatively uncomplicated coil arrangement in conjunction with a cylindrical shell made of iron which determines to a considerable degree the configuration of the magnetic field generated by the coils, a fact which is to be taken into account when designing the coils. Since heretofore electromagnets used in NMR tomography have generally taken the form of solenoids, the effect of shaping the magnetic field by the use of a cylindrical shell may at first be thought unfavorable. However, the cylindrical shell has the advantage that the return of the magnetic flux made possible by it results in a substantial reduction in energy consumption of the electromagnet. Furthermore, the cylindrical iron shell also functions as a shield against external magnetic fields and other electromagnetic radiation. In addition, the magnetic field produced by the electromagnet itself not only will be limited to the space encompassed by the cylindrical shell, but the high frequency field produced in NMR tomography will be prevented from being transmitted to the outside.

The primary advantage of using a stable cylindrical iron shell is, however, that a mechanically extremely sturdy structure is obtained which, moreover, is receptive to ease of manufacture. The high degree of stability is due to the absolute symmetry of the cylindrical shell with respect to both its axis and its cross-sectional midplane. This symmetry is maintained also at temperature changes. As a consequence, any dimensional changes due to temperature fluctuations fail to cause an appreciable disturbance in the homogeneity of the magnetic field. Thus, no elaborate means are needed for temperature compensation or the maintenance of a constant temperature. At the same time, the reduced energy requirements not only result in a lowering of operational costs, but also the degree of heating up of the coils is diminished so that the necessary cooling provisions may be simplified. Requisite to the high mechanical stability and the lowering in energy consumption, while at the same time providing effective shielding properties, is a cylindrical shell having a wall thickness such as is not usually required for simple shielding.

In the electromagnet according to the invention, coil systems may be made use of as they are described in Journal of Applied Physics, Vol. 40, No. 8 (July 1969), p. 3171–3179. Since these well known systems, however, also employ exclusively solenoids, the shape of the coils must be modified because of the use of a cylindrical iron shell. The particular dimensions may be computed numerically by computers. It is possible to use a field coil comprised of at least two constituent coils disposed at a defined distance from one another. With an appropriate dimensioning of the constituent coils and their spacing, any special correction or error coils may be omitted such as are being used in conjunction with the solenoids according to the above cited reference. However, it is also possible to dispose an error coil on at least one end of the field coil or the constituent coils, respectively, with the error coil preferably concentrically surrounding the field or constituent coils, resp.

In a preferred embodiment of the invention, the coils are wound on spools which are fastened to the inner surface of the cylindrical shell by spacer discs and are centered. This makes it possible to achieve an accurate coaxially and also thermically symmetric arrangement of the coils with respect to the cylindrical shell.

The effectiveness of the cylindrical shell both as a shield and a means to facilitate magnetic reflux may be further enhanced according to another embodiment of the invention by providing annular discs of iron at the end portion of the cylindrical shell to cover the front faces of the coils. It will be found that also these annular discs, like the cylindrical shell, must have a substantial thickness. The annular discs may also be utilized in the compensation of inhomogeneities of the magnetic field.

For the purpose of enhancing the magnetic field and also the shielding effect, it is desirable to provide the external surfaces of the annular discs with tubular projections or studs made of iron, the diameter of which is at the most equal to the diameter of the cylindrical shell. It will be understood that these studs are likewise carefully dimensioned rotation-symmetric structural elements, the design of which should be taken into account in the dimensioning of the coils.

Insofar as the intended use of the electromagnet will allow it, the cylindrical shell may be completely closed on at least one end by an iron closure member. Here again, the positioning and the shape of the iron closure member may be utilized to promote the homogeneity of the magnetic field generated, because the magnetic field will be reflected on the surface of the iron closure member, resulting in a seemingly doubling of the length of the coil which in turn leads to an increase in homogeneity of the magnetic field, coupled with a lowering in energy requirements. In a preferred embodiment of the invention, the iron cover member is curved to facilitate focussing of the magnetic field lines in the area adjacent the cover member, so as to aid in enhancing the homogeneity of the magnetic field.

Electromagnets according to the invention having a cylindrical shell which is open at least on one end are eminently suitable for examinations in which the longitudinal axis of the body to be examined is to coincide with the longitudinal axis of the electromagnet, so that the body may be introduced into the electromagnet from one end in the direction of its longitudinal axis. Both a standing and a reclined position of the electromagnet are feasible.

Another embodiment of the electromagnet according to the invention is especially suitable for examinations in which the longitudinal axis of the body to be examined is to be disposed transversely to the longitudinal axis of the electromagnet. The cylindrical shell in this instance is closed at both ends by cover members and is provided with an opening symmetric about its midplane so that the body to be examined may be introduced into the electromagnet transversely to the longitudinal axis of the electromagnet. In this embodiment, the field coil is comprised of symmetric constituent coils arranged on each side of the opening and preferably provided with an error coil at the end facing the opening.

Another embodiment of the electromagnet of the invention particularly suitable for examinations of a special nature is characterized by the feature that the cylindrical shell closed at one end by a cover member is lengthened at the other end to extend beyond the field coil. The section extending beyond the field coil is provided with an opening over the entire length thereof up to its terminal portion where it has a detachable closure member. In this embodiment, the detachable closure member may take the form of a seat. The vertically axially disposed cylindrical shell including the coil assembly may be mounted so as to be movable in the vertical direction. This embodiment of the invention enables the upper body portion of a seated person to be examined in an electromagnet, whereby the shielding is nearly complete.

As mentioned previously, the electromagnet may also include in addition to the field coil, correction or error coils which are concentrically disposed within or outside of the field coil (coaxial shim system) and which serve to improve the homogeneity and to produce special gradients of the magnetic field. In NMR tomography it is frequently necessary to provide a stepping of the gradients. In order to keep any resulting eddy currents, that may arise in the cylinder, as small as possible, the cylindrical shell, according to yet another embodiment of the invention, is provided along its longitudinal axial direction with one or a plurality of slots. This measure will prevent, at least, the creation of closed currents in the circumferential direction of the cylindrical shell.

The invention will be described in further detail with reference to exemplary embodiments illustrated in the drawings. The features described and illustrated in the specification and drawings may find application also in other embodiments of the invention and may be employed either individually or in any number in any desired combination.

DETAILED DESCRIPTION OF ILLUSTRATIVE EMBODIMENTS

Figure 1:
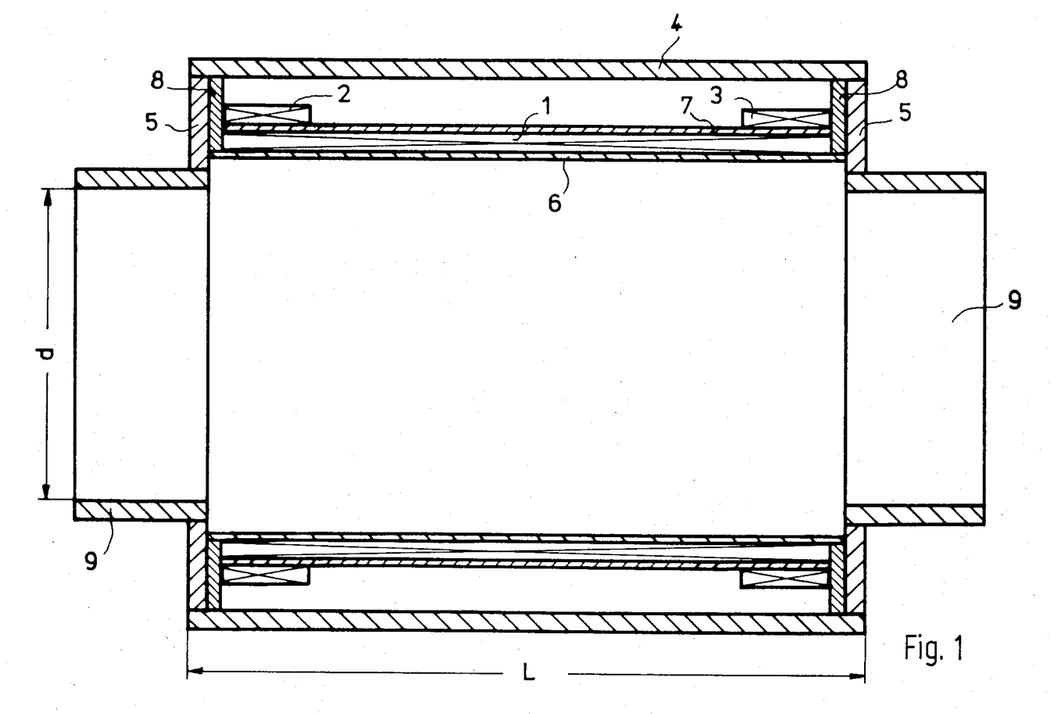
FIG. 1 is a longitudinal sectional view of a first embodiment of the electromagnet according to the invention.

The electromagnet illustrated in FIG. 1 comprises a cylindrical field coil 1 having correction or error coils 2 and 3 disposed at each end and concentrically surrounding the field coil 1. The coils 1 to 3 are enclosed in a cylindrical shell 4 made of soft iron, with a clearance between the inner surface of the shell and the coils 1 to 3. The length L of the cylindrical shell 4 slightly exceeds the length of the cylindrical coil 1. The coils 1 to 3 are wound upon cores 6 and 7 which are supported and simultaneously centered with respect to the cylindrical shell by spacer discs 8. It is also possible to have the annular iron discs 5 take over the function of supporting and centering the cores 6 and 7. The cores 6 and 7 and the spacer discs 8 are made of nonmagnetic materials, such as aluminum or bronze. Mounted in the openings of the annular disc 5 are tubular projections or studs 9, which are also made of iron and whose diameter is slightly less than the diameter of the cylindrical coil 1.

The length L of the cylindrical shell 4 and the interior diameter d of the tubular stud 9 are substantially determined by the dimensions of the body to be examined and the degree of homogeneity required of the magnetic field. Considering the dimensions involved in examining the human body, the space requirements of the electromagnet of FIG. 1 are relatively low, and in any event are substantially less than the space required for a conventional Helmholtz Double Coil apparatus.

The thick-walled cylindrical iron shell 4, in conjunction with the spacer discs 8, ensures a very secure and accurately centered mounting of the coils 1 to 3, which can be maintained also when there are temperature fluctuations triggering dimensional changes, because the system is completely symmetric. Consequently, the homogeneity of the magnetic field in the critical region is likewise preserved, so that no compensation measures are required. The reflux of the external magnetic field through the cylindrical iron shell 4 and the annular discs 5 results in a substantial reduction in energy requirements which is significant as to both operating costs and stability of the electromagnet. At the same time, the particular construction of the iron shell 4, notably the dimensioning of the annular discs 5 and the tubular studs 9, offers additional opportunities to supplement the effect of the error coils 2, 3 on the magnetic field to promote its homogeneity. Furthermore, the extremely thick-walled iron shell 4 has an excellent shielding effect against external magnetic fields and adverse external electromagnetic radiation as well as against radiation from the high frequency field generated in NMR tomography. Yet, the electromagnet is of a very straightforward mechanical construction, enabling cost efficient manufacture despite the necessity of maintaining very narrow tolerances. The necessary cooling may be effected in known manner by a cooling agent conducted either through cooling means which connect with the cores 6 and 7, or directly through a hollow core on which the coils are wound.

Figure 2:
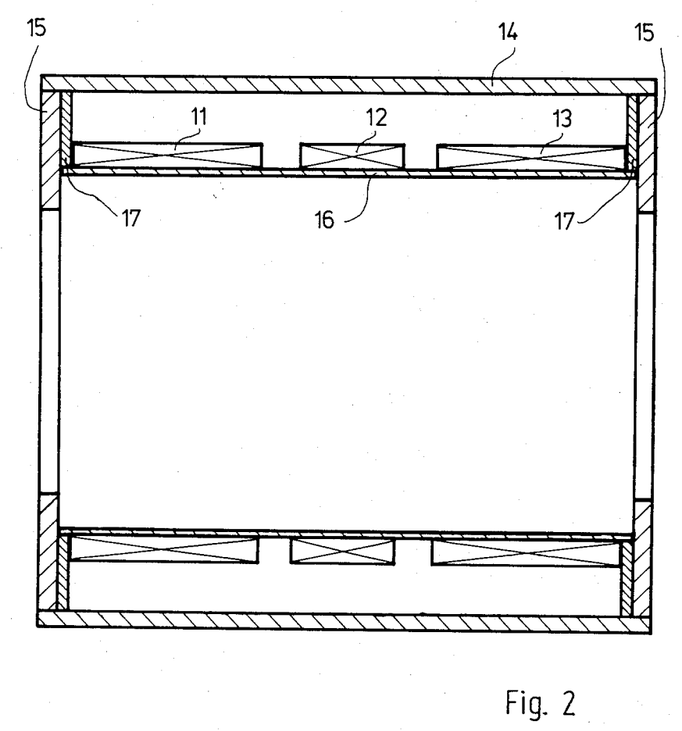
FIG. 2 is a longitudinal sectional view of a second embodiment of an electromagnet according to the invention.

In the embodiment shown in FIG. 2, the field coil is comprised of three constituent coils 11, 12, 13 wound upon a common core 16 at defined intervals. The core 16 bears against spacers 17 provided adjacent the cylindrical shell 14 and is centered. The cylindrical shell 14 and the annular discs 15 are made of iron and are provided with thick walls. These structural members constitute a vehicle for the reflux of the external magnetic field and at the same time form magnetic and electrical sheilding means. The constituent coils 11, 12 and 13 and the spacings therebetween, in conjunction with the measurements of the cylindrical shell 14 and the annular discs 15, are so dimensioned that a highly homogeneous magnetic field is created in the interior of the coil assembly. Here again, due to the extremely stable and symmetric structural arrangement, the electromagnet according to FIG. 2 has the same advantageous properties as the electromagnet of FIG. 1. The modified coil assembly permits a reduced structural length at the expense of a slightly higher power consumption.

Figure 3:
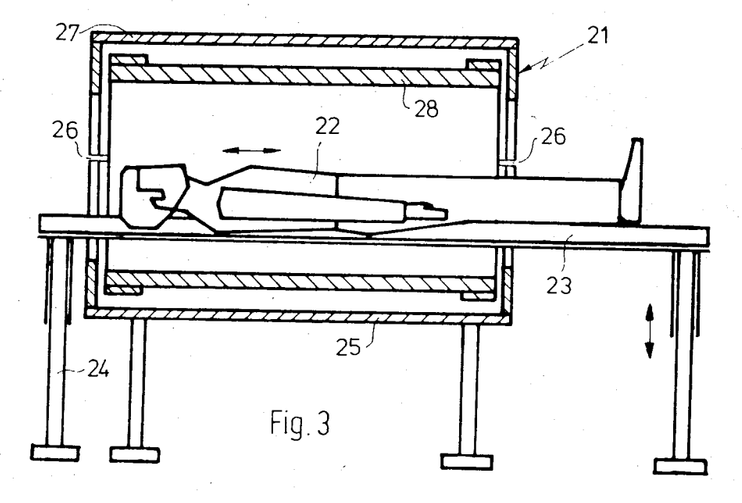
FIGS. 3 to 6 are schematic illustrations of various embodiments of the electromagnet according to the invention as employed in NMR tomography applied to the human body.

FIG. 3 illustrates the application of an electromagnet of the type shown in FIG. 1 in the examination of the human body. As will be apparent, the electromagnet 21 is so dimensioned that it is capable of accommodating essential portions of the human body 22. In the apparatus shown, the electromagnet 21 is disposed axially horizontally, and the human body 22 is lying on a table 23 which penetrates into the interior of the electromagnet and is adjustable as to height by means of telescopic legs 24. In addition, means may be provided for moving the table 23 in the direction of the longitudinal axis of the magnet 21. In this embodiment, the cylindrical shell 25 is provided with slots in two diametrically opposite places 26, allowing the upper half 27 of the cylindrical shell to be lifted from the lower half to expose for easy accessibility the exciter coil 28 and other parts located inside the cylinder. Moreover, the longitudinal slots 26 prevent the rise of closed currents along the circumferential direction of the cylindrical shell, as they may particularly occur when the error coils are connected or disconnected.

Figures 4, 5:
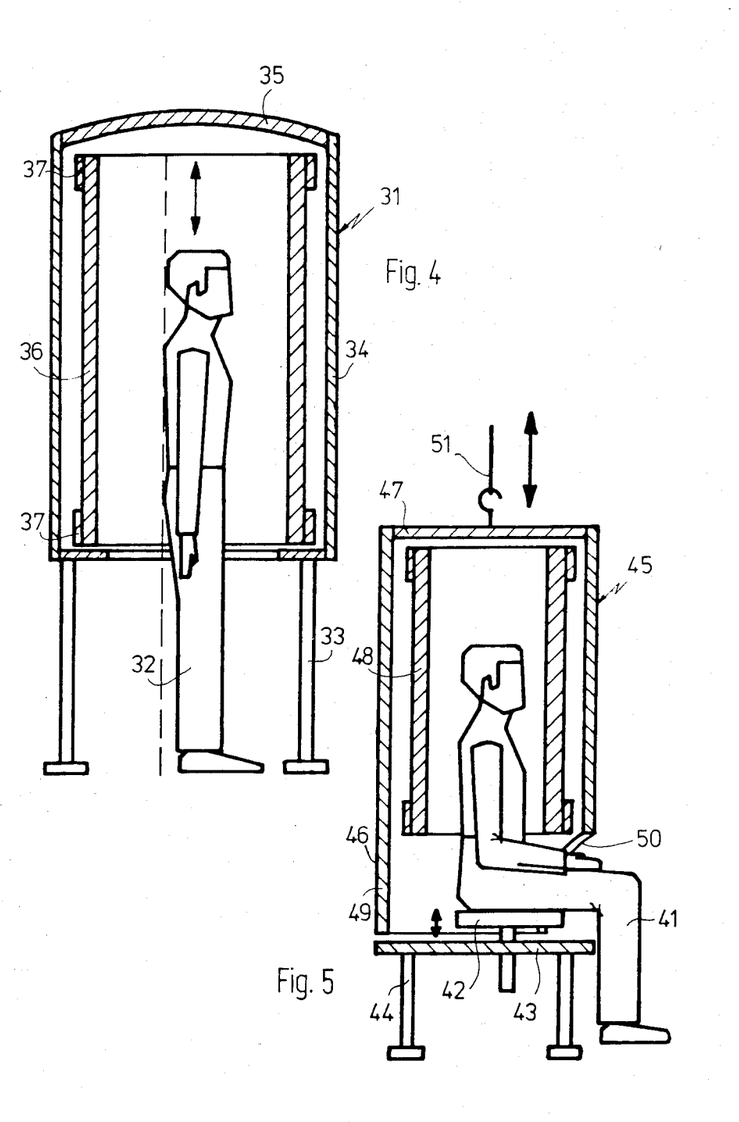

As shown in FIG. 4, it is principally possible to dispose an electromagnet 31 according to the invention also in vertical attitude so that the upper body portion of a standing patient 32 is surrounded by the electromagnet. In this embodiment, the electromagnet 31 is mounted with its bottom portion on uprights 33 which are of the telescopic type to raise the magnet 31 sufficiently for the patient to conveniently assume his position for examination, whereupon the electromagnet 31 is again lowered over the patient. Alternatively, the magnet may be raised or lowered by means of a pulley disc. In this embodiment, there is no need for the electromagnet 31 to be open at both ends. Therefore, the cylindrical iron shell 34 of the magnet is closed at the top by a cover member 35. The magnetic field will be reflected on the surface of this cover member and this has the effect that the coil is seemingly doubled in length, resulting in an enhancement of the homogeneity of the magnetic field and an accompanying reduction in energy requirements. The particular curving of the closure member 35 is highly advantageous because it promotes focussing of the field lines and thus an increase in the homogeneity of the field in the upper third of the magnet. It will be appreciated that also in this respect the effect that the cover member 35 has on the magnetic field must be taken into account in the design and dimensioning of the field coils and error coils 36, 37.

If the patient assumes a sitting position during examination, an electromagnet may be used which is closed on both ends, as it is illustrated in FIG. 5. This type of electromagnet enables the patient 41 to sit on a seat 42 provided on the upper surface of an iron plate 43 supported by legs 44 on the floor. The axially vertically disposed electromagnet 45 comprises a cylindrical shell 46 which is closed on top by an iron cover 47. An extension 49 forming part of the cylindrical shell 46 projects past the coil assembly 48 and bears against the edge of iron plate 43 when the electromagnet 45 is lowered. The section 49 extending past the coil assembly 48 has an opening 50 extending the whole length of it up to its edge. This opening 50 is large enough to allow the legs of the patient 41 to pass through. The electromagnet 45 may be raised from the iron plate 43 by means of a pulley 51 or the like to enable the patient 41 to conveniently enter and exit the magnet. When the electromagnet 45 is lowered, the iron plate 43 forms a closure member to close off the bottom of the electromagnet.

Figure 6:
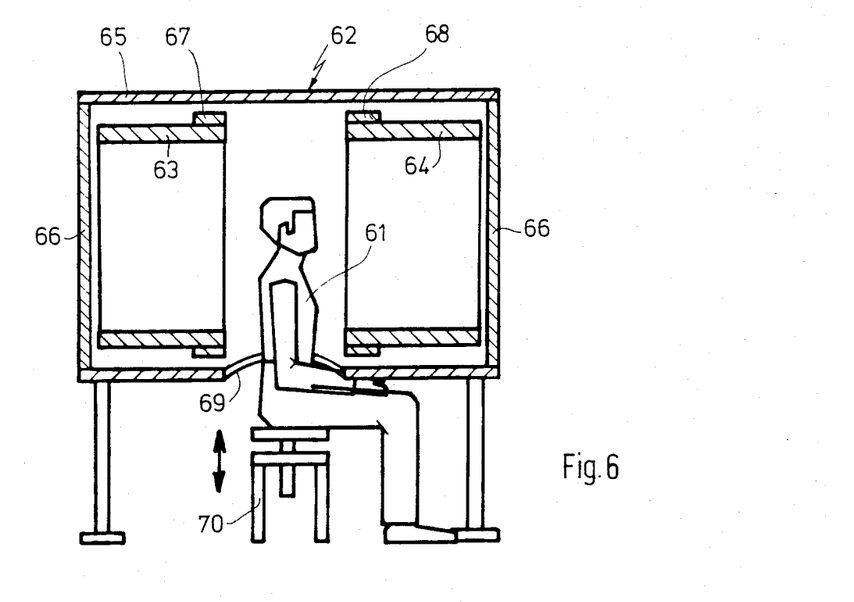

While in the previously described embodiments of the invention the longitudinal axis of the patient's body coincided with the longitudinal axis of the electromagnet, FIG. 6 illustrates an embodiment in which the upper part 61 of the patient's body extends into the electromagnet 62 transversely to the longitudinal axis of the electromagnet. In this embodiment of the invention, the electromagnet 62 is provided with a coil assembly comprising two constituent coils 63, 64, with a space therebetween to leave room for the upper part of the patient's body. The constituent coils 63, 64 are encompassed by the cylindrical shell 65 which is closed at both ends by closure members 66. Each of the constituent coils 63, 64 is concentrically surrounded by error coils 67, 68 resp. The cylindrical shell 65 has at its underside an opening 69 which is concentric to the transverse midplane of the cylindrical shell 65 and the diameter of which is approximately equal to the space between the coils 63, 64. Thus, the opening 69 is large enough for the upper portion of the patient's body to pass through. Again, the electromagnet 62 is adapted to be lowered over the patient's upper body and raised up again. The patient may be in a sitting position, as illustrated, or he may also be examined standing upright. It is aso possible to move the patient 61 from below into the interior of the electromagnet 62 by means of a chair 70 which is adjustable as to height.

It will be understood that the embodiments described in the foregoing represent but a few of many conceivable arrangements, the particular construction of which will depend on the type of application of the electromagnet, notably on the kind of body to be examined.

I claim:

1. An electromagnet for producing a constant magnetic field as required for use in NMR tomography of a body to be examined, said electromagnet including a hollow coil assembly for generating an at least approximately homogeneous magnetic field within said coil assembly, said coil assembly having a space therein adapted to receive the body to be examined, said coil assembly comprising at least one cylindrical field coil having a circular cross-section and at least one error coil concentrically disposed around said field coil, a stable cylindrical shell made of iron and concentrically surrounding said field coil and said error coil, and supporting means supported by said cylindrical shell for supporting said coils, said shell affording a return magnetic path for the magnetic field of said coils and cooperating with said coils to afford a magnetic field of enhanced homogeneity within said coil assembly.

2. An electromagnet according to claim 1,
   including cores upon which said coils are wound,
   said supporting means comprising annular spacer discs mounted between said cylindrical shell and said cores and concentrically supporting said cores and said coils within said shell.

3. An electromagnet according to claim 1,
   comprising annular iron discs disposed at the opposite end portions of said cylindrical shell and covering the corresponding ends of said coils.

4. An electromagnet according to claim 1,
   including cylindrical cores upon which said coils are wound,
   and annular iron discs connected to the opposite ends of said cylindrical shell and covering the corresponding ends of said coils,
   said iron discs constituting said supporting means for supporting and centering said cores and said coils within said cylindrical shell.

5. An electromagnet according to claim 3,
   comprising tubular projections made of iron and projecting axially from said respective annular iron discs in exterior directions away from the corresponding ends of said coils,
   said tubular projections having a diameter which is at the most equal to the inner diameter of said field coil.

6. An electromagnet according to claim 1,
   said cylindrical shell having an iron cover closing at least one end of said shell.

7. An electromagnet according to claim 6,
   in which said iron cover is outwardly convex.

8. An electromagnet according to claim 1,
   said cylindrical shell having a first iron cover closing one end of said shell,
   said cylindrical shell having an end section at the opposite end of said shell and extending beyond said field coil,
   said end section having an end opening therein,
   said cylindrical shell having a second iron end cover for disengageably covering said end opening in said end section,
   said end section having a lateral opening therein for admitting a portion of the body to be examined.

9. An electromagnet according to claim 8,
   in which said second iron end cover comprises a seat,
   said cylindrical shell and said coil assembly having a common axis disposed vertically,
   said cylindrical shell and said second end cover being relatively movable vertically between separated and engaged positions to facilitate the admission of the body portion to be examined.

10. An electromagnet according to claim 1,
    in which said cylindrical shell is provided with at least one longitudinal slot.

11. An electromagnet according to claim 1, in which said cylindrical shell is provided with a pair of longitudinal slots whereby said shell is split longitudinally into two separable sections.

12. An electromagnet according to claim 1, said coil assembly comprising a single cylindrical field coil and a pair of error coils concentrically disposed around opposite end portions of said field coil.

13. An electromagnet for producing a constant magnetic field as required for use in NMR tomography of a body to be examined,
   said electromagnet including a hollow coil assembly for generating an at least approximately homogeneous magnetic field within said coil assembly,
   said coil assembly having a space therein adapted to receive the body to be examined,
   said coil assembly comprising a cylindrical field coil having a circular cross-section and including at least two constituent coils spaced apart axially at predetermined positions,
   a stable cylindrical shell made of iron and concentrically surrounding said coils,
   and supporting means supported by said cylindrical shell for supporting said coils,
   said shell affording a return magnetic path for the magnetic field of said coils and cooperating with said coils to afford a magnetic field of enhanced homogeneity within said coil assembly.

14. An electromagnet according to claim 13, comprising a plurality of error coils concentrically disposed around said field coil.

15. An electromagnet according to claim 13, comprising a pair of iron cover members closing the opposite ends of said cylindrical shell,
   said shell having an opening which is symmetrical about its transverse midplane,
   said field coil comprising two of said constituent coils symmetrically disposed on opposite sides of said opening.

16. An electromagnet according to claim 15, comprising two error coils concentrically disposed around said respective two constituent coils at the ends thereof facing said opening.

17. An electromagnet for producing a constant magnetic field as required for use in NMR tomography of a body to be examined,
   said electromagnet including a hollow coil assembly for generating an at least approximately homogeneous magnetic field within said coil assembly,
   said coil assembly having a space therein adapted to receive the body to be examined,
   said coil assembly comprising at least one cylindrical field coil having a circular cross-section,
   a stable cylindrical shell made of iron and concentrically surrounding said field coil,
   and supporting means supported by said cylindrical shell for supporting said coil,
   said shell affording a return magnetic path for the magnetic field of said coil and cooperating with said coil to afford a magnetic field of enhanced homogeneity within said coil assembly,
   said cylindrical shell having an iron cover closing at least one end of said shell.

18. An electromagnet according to claim 17, in which said iron cover is outwardly convex.

19. An electromagnet according to claim 17, said cylindrical shell having first and second iron covers,
   said first iron cover closing one end of said shell,
   said cylindrical shell having an end section at the opposite end of said shell and extending beyond said field coil,
   said end section having an end opening therein for disengageably receiving said second iron cover.

20. An electromagnet according to claim 19, said end section having a lateral opening therein for admitting a portion of the body to be examined,
   said second iron cover comprising a seat,
   said cylindrical shell and said coil assembly having a common axis disposed vertically,
   said cylindrical shell and said second iron cover being relatively movable vertically between separated and engaged positions to facilitate the admission of the body portion to be examined.

* * * * *